(12) United States Patent
Burrell et al.

(10) Patent No.: US 6,333,093 B1
(45) Date of Patent: *Dec. 25, 2001

(54) ANTI-MICROBIAL COATINGS HAVING INDICATOR PROPERTIES AND WOUND DRESSINGS

(75) Inventors: Robert Edward Burrell, Sherwood Park; Roderick John Precht, Edmonton, both of (CA)

(73) Assignee: Westaim Biomedical Corp., Fort Saskatchewan (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/818,869

(22) Filed: Mar. 17, 1997

(51) Int. Cl.[7] ....................................... B32B 23/02
(52) U.S. Cl. .................... 428/194; 428/198; 428/221; 428/328; 428/354
(58) Field of Search ..................... 156/164, 291, 156/163, 324, 183, 229; 428/194, 198, 221, 328, 354

(56) References Cited

U.S. PATENT DOCUMENTS

| | | | |
|---|---|---|---|
| 2,590,906 | 4/1952 | Tripp | 88/110 |
| 3,811,752 | 5/1974 | Jaklevic et al. | 350/164 |
| 4,170,460 | 10/1979 | Donley | 65/30 |
| 4,702,955 | 10/1987 | Allred et al. | 428/213 |
| 4,728,323 | 3/1988 | Matson | 604/304 |
| 4,820,649 | 4/1989 | Kawaguchi et al. | 436/501 |
| 4,844,965 | 7/1989 | Foxman | 428/91 |
| 4,860,737 | 8/1989 | Lang et al. | 128/156 |
| 4,874,664 | 10/1989 | Hamaguchi et al. | 428/325 |
| 4,891,113 | 1/1990 | Criss | 204/192.15 |
| 4,902,581 | 2/1990 | Criss | 428/627 |
| 4,931,384 | 6/1990 | Layton et al. | 435/7 |

(List continued on next page.)

FOREIGN PATENT DOCUMENTS

| | | |
|---|---|---|
| 0 255 248 | 2/1988 | (EP). |
| 0 395 300 | 10/1990 | (EP). |
| 0 430 608 | 6/1991 | (EP). |
| 2 063 920 | 6/1981 | (GB). |
| 2281212A * | 1/1995 | (GB). |
| 63 078 051 | 4/1988 | (JP). |
| WO 92/11043 | 7/1992 | (WO). |
| WO 93/23092 | 11/1993 | (WO). |
| WO 95/13704 | 5/1995 | (WO). |

*Primary Examiner*—Merrick Dixon
(74) *Attorney, Agent, or Firm*—Finnegan, Henderson, Farabow, Garrett & Dunner, L.L.P.

(57) ABSTRACT

Multilayer anti-microbial materials formed to produce an interference colour, and thus an indictor of anti-microbial effect, are provided. The materials include a partly reflective base layer and a partly reflective, partly transmissive top layer balanced to produce an interference colour. The top layer is formed from an anti-microbial metal with atomic disorder. Dissolution or a change in composition of the top layer on contacting an alcohol or electrolyte causes a change in optical path length so as to produce a change in the interference colour of the material. Multilayer, laminated wound dressings are also provided. The dressing includes a first and second layer, and preferably a third layer. The first and third layers are formed of perforated, non-adherent materials and most preferably carry an anti-microbial coating as above. The second layer is sandwiched between the first and third layers and is formed of an absorbent material. At least one of the layers is formed from a plastic material. The layers are laminated together by ultrasonic welds spaced intermittently on the dressing to allow the dressing to be cut to size with delaminating.

44 Claims, 1 Drawing Sheet

U.S. PATENT DOCUMENTS

| | | | |
|---|---|---|---|
| 4,937,274 | 6/1990 | Arima et al. | 523/220 |
| 4,943,484 | 7/1990 | Goodman | 428/441 |
| 4,964,963 | 10/1990 | Criss | 204/192.27 |
| 5,085,653 | 2/1992 | Levy | 604/358 |
| 5,124,172 | 6/1992 | Burrell et al. | 427/2 |
| 5,147,338 | 9/1992 | Lang et al. | 604/304 |
| 5,227,168 | 7/1993 | Chvapil et al. | 421/445 |
| 5,271,994 | 12/1993 | Termath | 428/216 |
| 5,376,431 | 12/1994 | Rowland | 428/164 |
| 5,405,644 | 4/1995 | Ohsumi et al. | 427/2.31 |
| 5,437,621 | 8/1995 | Andrews et al. | 602/42 |
| 5,454,886 | 10/1995 | Burrell et al. | 148/565 |
| 5,465,735 | 11/1995 | Patel | 128/888 |
| 5,510,163 | 4/1996 | Sullivan et al. | 428/64.1 |

\* cited by examiner

ANTI-MICROBIAL COATINGS HAVING INDICATOR PROPERTIES AND WOUND DRESSINGS

FIELD OF THE INVENTION

The invention relates to anti-microbial coatings formed from one or more anti-microbial metals and to multilayer laminated wound dressings.

BACKGROUND OF THE INVENTION

Burns and related wounds present a serious problem in infection control. Noble metal ions such as silver and gold ions are known for their anti-microbial activity and have been used in medical care for many years to prevent and treat infection. Water soluble silver nitrate has been widely used as an astringent and as a potent anti-microbial solution. For example, 10% silver solution preparations are applied directly to ulcers of the mouth; dressings wetted with 0.5% silver nitrate solutions are used to cover second and third degree burns, especially to protect against gram negative infections; and drops of a 1% silver nitrate solution in the eye is still a legally required treatment in many areas of the world for prophylaxis of ophthalmia neonatorum.

The anti-microbial effect of these known silver nitrate solutions appears to be directly related to the concentration of the silver ions. Unfortunately, water soluble silver nitrate solutions provide very little residual activity due to the reactivity of silver ions with chloride, etc. in body fluids. To compensate for this lack of in use longevity, soluble silver solutions, such as silver nitrate, are used at far higher concentrations (3000 to 3500 mg/L) than are required for bacterial control (2 to 5 mg/L) in an effort to extend the duration of the antimicrobial effect. As a result, the solution can have irritating and astringent effects on wounds. For instance 1% solutions used prophylactically for ophthalmia neonatorum must be followed in a few seconds with a 0.85% sodium chloride rinse to prevent conjunctivitis. Burn wound treatment in current use for second degree burns employs 0.5% silver nitrate solutions which must be added frequently throughout the day (usually 12 times daily) in order to replenish the active $Ag^+$ ion. Also in use are silver sulphadiazine creams, which need frequent reapplication and scraping to remove the debris and chemical barrier, and which may also cause sensitivity or allergic reaction to the sulpha component.

Significant improvements to minimize adverse properties have been sought since the turn of the century. Some efforts have focussed on the use of colloidal solutions of insoluble, poorly ionized salts such as oxide complexes with proteins to reduce the rate of release of silver ions. Other efforts focussed on producing silver in an activated form, for example by depositing it on porous carbon to provide slower release of silver ions, or by activating the silver after deposition, for example by treatment with strong oxidizing agents. Still other efforts were directed at electrical activation of the silver coatings to drive the release of silver, or depositing with an electochemically different, more noble metal so as to use dual metal galvanic action as the driving force to release silver ions. To date, improvements in anti-microbial agents derived from anti-microbial metals such as silver, and wound treatment procedures using same are sought to improve the anti-microbial efficacy of the metal ions, to reduce the frequency of the application of the anti-microbial agent, and to improve infection control in wound treatment. Also needed is a visible indicator of the anti-microbial activity and effect, so as to minimize over application of the anti-microbial agents and unnecessary wound dressing removal, and thus improve patient comfort and minimize sensitivity reactions to anti-microbial metals.

Applicants have developed anti-microbial materials which provide efficacious and sustainable anti-microbial effect. Such materials are described in, for example U.S. Pat. No. 5,454,886, issued Oct. 3, 1995, to Burrell et al. The materials are formed as powders, foils, flakes, coatings or thin films from one or more anti-microbial metals so as to contain atomic disorder.

SUMMARY OF THE INVENTION

The inventors made a number of surprising discoveries when working on improvements to the anti-microbial materials formed with atomic disorder described in their previous patent applications. Firstly, they discovered that a thin film of an anti-microbial metal material on a reflective base layer coating, such as a reflective silver coating, was capable of producing an interference colour. By altering the refractive index and/or the thickness of the top layer, different, discernible interference colours were produced. Secondly, they discovered that if the top anti-microbial metal layer was formed with atomic disorder so as to produce an anti-microbial effect when exposed to alcohol or electrolyte, sharp interference colours were produced, providing a useful indicator of activation (release of ions etc.) from medical devices and the like carrying such a coating. Even minor dissolution or composition changes of the top layer of the coating, such as a fingertip touch, was discovered to cause a detectable colour change. Thirdly, they discovered that a single layer of an anti-microbial metal formed with atomic disorder could be produced with an initial colour which changed on contacting an alcohol or electrolyte so as to generate an interference colour which was different from the initial colour. Without being bound by the same, it is believed that contacting the atomically disordered material forms a thin layer at the top of the material (hereinafter termed as "in situ generated top layer") which has a composition different enough from the underlying base layer that it is capable of providing an interference colour. Thus, the present invention extends to a method of indicating exposure of multilayer anti-microbial material formed with atomic disorder to an alcohol or electrolyte through the use of interference colours.

In one broad aspect, the invention provides a multilayer anti-microbial material comprising a) a base layer of a partly reflective material capable of generating an interference colour when covered with a partly reflective, partly light transmissive top layer; and b) a top layer formed over said base layer, said top layer being a partly reflective, partly light transmissive thin film containing at least one anti-microbial metal and having a thickness such that an interference colour is produced, said top layer having a refractive index different from that of the base layer, and the anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis. The invention extends to anti-microbial materials in which the top layer is formed above the base layer by such techniques as vapour deposition, and to materials having an in situ generated top layer.

The base layer might be provided as a substrate (ex. medical device) which is partly reflective such that it can provide an interference colour when covered with a partly reflective, partly transmissive top layer. Preferably the base layer is formed from a metal selected from Ag, Au, Pt, Pd, Cu, Ta or Al, with Au, Ag, Pt, Pd and Cu being most preferred. Preferably both the top and base layers are formed from anti-microbial metals formed with atomic disorder. The top layer is most preferably formed from Au or Ag.

Most preferably, the top layer is a composite material formed by depositing the anti-microbial metal in a matrix with atoms or molecules of a different material, wherein the different material provides atomic disorder in the matrix. The different material may be a biocompatible metal such as Ta, Ti, Nb, V, Hf, Zn, Mo, Si or Al, or oxides, nitrides, carbides, borides, halides, sulphides or hydrides of such biocompatible metals. Alternatively, the different material may be atoms or molecules absorbed or trapped from the atmosphere used in a vapour deposition process, including oxygen, nitrogen, hydrogen, boron, sulphur or halogens. As a further alternative, the different material may be an oxide, nitride, carbide, boride, halide, sulphide or hydride of an anti-microbial metal. Most preferably, the top layer is formed with Ag as the matrix metal, and either or both or silver oxide and absorbed or trapped oxygen as the different material.

The base layer, when provided as a coating on a substrate, is preferably at least 25 nm thick and more preferably at least 60 nm thick. If formed from an atomically disordered anti-microbial metal, the base layer is preferably between about 300 and 2500 nm thick so as to provide a prolonged anti-microbial effect after the top layer is dissolved. The top layer is preferably less than 400 nm thick and is more preferably between 5 and 210 nm thick. Most preferably, the top layer is between 40 and 160 nm thick.

The invention also extends to a process for producing a multilayer anti-microbial material capable of indicating exposure to an alcohol or a water based electrolyte. The process includes a) providing a base layer of a partly reflective material capable of generating an interference colour when covered with a partly reflective, partly light transmissive top layer; and b) providing a top layer over said base layer, said top layer being a partly reflective, partly light transmissive thin film containing at least one anti-microbial metal and having a thickness such that an interference colour is produced, said top layer having a refractive index different from that of the base layer, and said anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis. The top layer can be provided by depositing it above the base layer, for instance by vapour deposition, or the top layer can be provided as an in situ generated top layer. In either process, a colour change occurs on contact with an alcohol or water based electrolyte so as to indicate activation of the material.

The inventors also discovered, when working with wound dressings materials that multilayer wound dressings could be laminated together with the use of ultrasonic welding at intermittent locations, to produce a wound dressing which could be conveniently cut to size, without causing delamination of the layers, and without having to resort to the use of stitching or adhesives to bind the layers together. The presence of the ultrasonic welds at intermittent locations on the dressing was surprisingly advantageous over stitched dressings or the use of adhesives, since the ultrasonically welded dressings were found to have excellent conformability properties (i.e. ability to conform to wound and skin contours). In wound dressings having one or more perforated layers to allow for fluid penetration, the ultrasonic welds were also found to only minimally interfere with penetrability properties of the dressings. Importantly, when wound dressings were coated with anti-microbial metal coatings of this invention, that is dressings which included a coating of one or more layers of an anti-microbial metal formed with atomic disorder, ultrasonic welding to laminate layers of the wound dressing was found not to inhibit anti-microbial activity. Atomic disorder in a material is easily removed when heat is applied to the material, since heat can anneal out crystalline defects.

Thus, in another broad aspect, the invention provides a multilayer, laminated wound dressing, including:

a first, wound facing layer formed of a perforated, non-adherent material;

a second layer laminated to the first layer, and being formed of an absorbent material;

an optional third layer laminated to one or both of the first and second layers;

at least one of the first, second and optional third layers, being formed from a plastic material; and the first, second and optional third layers being laminated together by ultrasonic welds spaced intermittently on the dressing so as to allow the dressing to be cut down in size without causing delamination.

The wound dressing is preferably formed with an anti-microbial coating which is most preferably the multilayer anti-microbial material set out above, so as to provide an interference colour indicator of activation on contacting an alcohol or a water based electrolyte.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Anti-microbial metals" are metals whose ions have an anti-microbial effect. Preferably, the metal will also be biocompatible. Preferred anti-microbial metals include Ag, Au, Pt, Pd, Ir (i.e. the noble metals), Sn, Cu, Sb, Bi and Zn.

"Biocompatible" means non-toxic for the intended utility. Thus, for human utility, biocompatible means non-toxic to humans to human tissues.

"Anti-microbial effect" means that atoms, ions, molecules or clusters of the anti-microbial metal (hereinafter "species" of the anti-microbial metal) are released into the alcohol or electrolyte which the material contacts in concentrations sufficient to inhibit bacterial (or other microbial) growth in the vicinity of the material. The most common method of measuring anti-microbial effect is by measuring the zone of inhibition (ZOI) created when the material is placed on a bacterial lawn. A relatively small or no ZOI (ex. less than 1 mm) indicates a non useful anti-microbial effect, while a larger ZOI (ex. greater than 5 mm) indicates a highly useful anti-microbial effect. One procedure for a ZOI test is set out in the Examples which follow.

"Sustained release" or "sustainable basis" are used to define release of atoms, molecules, ions or clusters of an anti-microbial metal that continues over time measured in hours or days, and thus distinguishes release of such metal species from the bulk metal, which release such species at a rate and concentration which is too low to achieve an anti-microbial effect, and from highly soluble salts of anti-microbial metals such as silver nitrate, which releases silver ions virtually instantly, but not continuously, in contact with an alcohol or electrolyte.

"Atomic disorder" includes high concentrations of: point defects in a crystal lattice, vacancies, line defects such as dislocations, interstitial atoms, amorphous regions, gain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder i.e. which freeze-in atomic disorder, means diffusion of atoms and/or molecules on the surface or in the matrix of the material being formed.

"Substrate" means any surface, usually that of a medical device, which is itself partly reflective, or which can be coated with a partly reflective metal coating by such techniques vapour deposition including evaporation or physical vapour deposition. In this application, it should be understood that when it is stated that a reflective base layer is provided on a substrate, it does not mean that every substrate needs to have such a layer formed thereon, but is meant to include a substrate which is inherently reflective, such as for instance reflective plates or instruments formed of polymers, metals or dielectrics, such that it can provide an interference colour.

"Medical device" means any device, appliance, fixture, fibre, fabric or material intended for a medical, health care or personal hygiene utility, including, without limitation orthopaedic pins, plates, implants, tracheal tubes, catheters, insulin pumps, wound closures, drains, shunts, dressings, connectors, prosthetic devices, pacemaker leads, needles, dental prostheses, ventilator tubes, surgical instruments, wound dressings, incontinent pads, sterile packaging clothing footwear, personal hygiene products such as diapers and sanitary pads, and biomedical/biotechnical laboratory equipment such as tables, enclosures and wall coverings and the like. Medical devices may be made of any suitable material, for example metals, including steel, aluminum and its alloys, latex, nylon, silicone, polyester, glass, ceramic, paper, cloth and other plastics and rubbers. For indwelling medical devices, the device will be made of a bioinert or biocompatible material. The device may take on any shape dictated by its utility, ranging from flat sheets to disc, rods and hollow tubes. The device may be rigid or flexible, a factor dictated by its intended utility.

"Alcohol or water based electrolyte" is meant to include any alcohol or water based electrolyte that the anti-microbial materials of the present invention might contact in order to activate (i.e cause the release of species of the anti-microbial metal) into same. The term is meant to include alcohols, water, gels, fluids, solvents, and tissues containing water, including body fluids (for example blood, urine or saliva), and body tissue (for example skin, muscle or bone).

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the anti-microbial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Wound" means cut, lesion, burn or other trauma to human or animal tissue requiring a wound dressing.

"Wound dressing" means a covering for a wound.

DESCRIPTION OF THE PREFERRED EMBODIMENTS

1. Multilayer Anti-Microbial Materials With Interference Colour

The invention provides anti-microbial materials formed with at least two layers, a base layer and a top layer, so as to produce an interference colour. Both layers are partly reflective; the top layer is partly light transmissive. The top layer is a thin film containing at least one anti-microbial metal formed with sufficient atomic disorder such that the top layer, in contact with an alcohol or water based electrolyte, releases ions, atoms, molecules or clusters of the anti-microbial metal at a concentration sufficient to provide a localized anti-microbial effect on a sustainable basis. In this way, the top layer, in contact with the alcohol or electrolyte, will undergo a change in optical path length, either by a change in thickness resulting from some dissolution, or through a change in the refractive index of the top layer resulting from a change in the composition of a newly formed thin layer formed on the top layer. Either or both of these results are sufficient to cause a detectable colour change, thus providing an indicator that the top coating has been activated.

The generation of interference colours is known in the art for decorative effects, diffraction gratings and diagnostic assay techniques, and thus the properties of at least two layers of materials necessary to generate an interference colour, that is the balance of reflectance, transmittance, layer thicknesses, and refractive indices of the layers, are generally well known in the art. The prior art has generally taught one to anodize a metal to produce a thin layer of a generally transparent oxide above a reflective base metal (see for example U.S. Pat. No. 5,124,172 issued Jun. 23, 1992 to Burrell et al.). Other prior art has taught sputter coating certain reflective metals with oxides of same or different metals in order to generate interference colours (see for example U.S. Pat. No. 4,702,955, issued Oct. 27, 1987, to Allred et al.). However, not all metals are easily anodizable. Furthermore, the art teaches that sputtering of such important anti-microbial metal oxides as silver oxide, is not possible without decomposition (see for example U.S. Pat. No. 4,728,323 issued Mar. 1, 1988, to Matson). Thus, novel procedures for producing anti-microbial materials capable of producing interference colours and an indication of generation of an anti-microbial effect, are set out herein.

Figure 1:
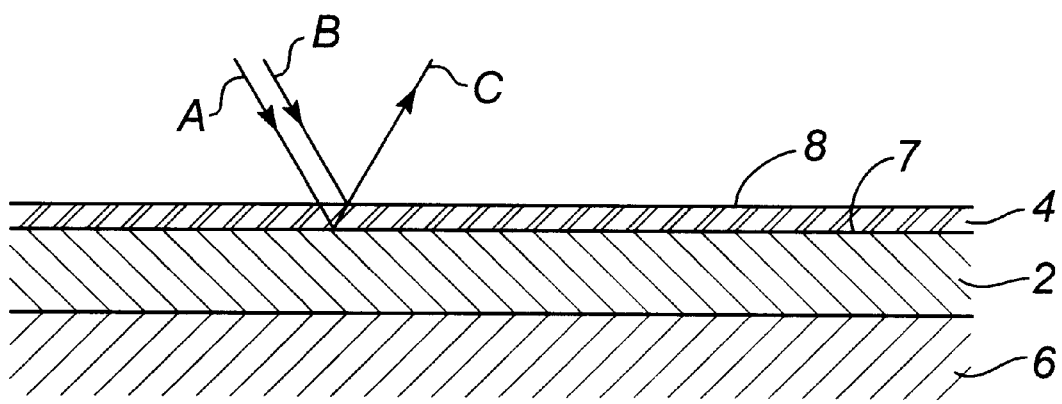
FIG. 1 is a schematic sectional figure of a coloured anti-microbial coating of this invention showing the generation of an interference colour.

The anti-microbial materials of this invention and the generation of an interference colour are shown schematically in FIG. 1. The material includes a base layer 2 and a top layer 4 over the base layer 2. The base and top layers 2, 4 are generally provided on a substrate 6, such as the surface of a medical device. However, if the substrate is itself partly reflective, the substrate can serve as the base layer. Both the base layer 2 and the top layer 4 are formed from a partly reflective material. In this way, at least a portion of the incoming light is reflected from the surface of the layer while another portion is transmitted through the layer. The top layer 4 is partly light transmissive to allow incident light to reach the interface with the base layer 2. The top layer 4 thus cannot approximate 100% reflectivity, such as in pure Al or Ag, or interference colours cannot be generated, as is well known in the art. The materials for layers 2, 4 should be balanced in their reflectances in order to generate an interference colour. Generally, the top layer 4 is deposited as a thin film having a thickness which maintains adequate transmittance to generate an interference colour. Furthermore, the refractive index for the materials in layers 2, 4 is different, accomplished by differences in their actual or effective compositions. For instance different materials in the two layers will result in the materials having different actual refractive indexes. However, if it is desired to make the layers 2, 4 from the same material, the layers can be deposited with different porosities or different levels/types of atomic disorder, in order to achieve different effective compositions, and thus different refractive indexes.

In this manner, in FIG. 1, incoming light A reflects off the interface 7 of the base and top layers 2, 4. Incoming light B reflects from the interface 8 of the top layer 4 with air, and interferes with the light reflected from the interface 7, so as to generate an "interference colour" C. The particular colour which is generated and its brightness will depend on the properties of the layers 2, 4, most importantly on the composition of the layers, which determines its transmittance and absorption properties, along with its refractive index, and on the thickness of the layers. Generally, it is desirable to generate first and second order interference colours, by limiting the thickness of the base layer and top layers to minimize the number of internal reflections. First and second order interference colours are generally brighter than third and fourth order etc. colours, making them more aesthetically pleasing, more consistently reproducible in manufacturing, and more susceptible to detectable colour change on variations in thickness on dissolution of even a minor amount of the top layer 4.

The property which determines the particular colour which is generated is the effective optical thickness of the top layer 4, that is the product of the refractive index of the top layer material and the actual thickness of the top layer 4. Thus the colour which is desired can be altered by changing the actual thickness or the top layer 4 or its refractive index.

In accordance with the invention, the base layer 2 is a partly reflective material capable of generating an interference colour when covered with a partly reflective, partly transmissive top layer 4. Reflective materials such as polymers, dielectrics or metals may be used in the base layer. To achieve the desired level of reflectance, the base layer 2 may be coated with an additional layer (not shown) to change its reflectance. For instance, a reflective plastic plate might be coated with a discontinuous (islands) or continuous thin coating of a reflective metal such as silver to produce a base layer whose average reflectance could be better balanced with that of the top layer to generate the desired interference colour effect. Preferably, the material in the base layer 2 is a reflective metal. Such metals are known in the art and include, for example one or more of the valve metals, e.g. Ta, Nb, Ti, Zr and Hf, as well as transition metals such as Au, Ag, Pt, Pd, Sn, Cu, V, W and Mo, or the metal Al. More preferably, the base material is formed from Ag, Au, Pt, Pd, Cu, Ta and Al. Use of a metal such as tantalum as the base layer 2 may cause reduction of oxide containing materials in the top layer 4. To avoid this, a barrier layer (not shown), such as tantalum oxide formed by anodizing at least a portion of the top surface of the Ta metal, should be included above a tantalum layer. Preferred metals for the base layer 2 are the anti-microbial metals Au, Ag, Pt, Pd, Sn and Cu, most preferably Au, Pt and Ag, in a partly reflective form.

The base layer 2 may be formed by known techniques, such as the vapour deposition techniques of evaporation or physical vapour deposition. Preferably, the base layer 2 is formed as a thin film by physical vapour deposition with atomic disorder, as set out below and in the inventors' previous patent applications, for example U.S. Pat. No. 5,454,889, in order to produce a sustainable anti-microbial effect when the base layer is ultimately exposed to an alcohol or water based electrolyte. The thickness of the base layer 2 is generally not critical, provided that it is partly reflective. Preferred thicknesses will vary widely with the material composition and the desired colour. However, in that the layer 2 is preferably a thin film formed by physical vapour deposition techniques, it should be at least about 25 nm thick to create a useful colour. To generate first and second order interference colours and to produce an anti-microbial effect in accordance with the preferred aspects of the invention, the base layer 2 should be greater than 60 nm thick, more preferably 300 to 2500 nm thick, and most preferably 600 to 900 nm thick.

The top layer 4 is formed of a partly reflective, partly light transmissive thin film containing at least one anti-microbial metal formed with atomic disorder so as to produce a sustainable anti-microbial effect, and ultimate colour change, when exposed to an alcohol or a water based electrolyte. The anti-microbial metal is preferably one or more of Ag, Au, Pt, Pd, Ir, Sn, Cu, Sb, Bi, and Zn in a partly reflective, partly transmissive form. More preferably, the anti-microbial metal is Ag, Au, Pt, Pd or Cu. The thickness of the top layer 4 formed from these metals is preferably less than 400 nm in order to maintain the preferred level of light transmission. The desired thickness will vary with the composition of the top layer 4, and with the desired end colour and colour change. For first and second order interference colours, the thickness will generally be less than about 400 nm. More preferably, the thickness will range from 5 to 210 nm, most preferably from 10 to 100 nm.

The top layer 4 may be a thin film of the base layer material, formed with a different refractive index for instance by altering the deposition conditions to change the porosity, composition and/or degree of atomic disorder in the layers 2, 4.

When the base layer 2 is itself formed from an anti-microbial metal with atomic disorder, the top layer 4 may be provided as an in situ generated top layer by virtue of its thickness and/or composition changing on contacting an alcohol or water based electrolyte, so as to produce an interference colour which differs from the initial colour of the base layer 2.

Most preferably, the top layer 4 is a thin film of a composite material formed by co-, sequentially or reactively depositing an anti-microbial metal in a matrix with atoms or molecules of a different material to create atomic disorder in the matrix, in the manner set out below. The different material is selected from a) biocompatible metals, b) oxygen, nitrogen, hydrogen, boron, sulphur or halogens, or c) an oxide, nitride, carbide, boride, halide, sulphide or hydride of either or both of an anti-microbial metal or a biocompatible metal. Most preferably, the top layer material is a composite material containing silver, and one or both of silver oxide and atoms or molecules containing oxygen trapped or absorbed in the silver matrix. The term "silver oxide" is meant to include any oxide or mixture of oxides of silver. However, the top layer 4 is preferably not formed solely of AgO and/or $Ag_2O$, since the solubility of these materials is low for providing a useful anti-microbial effect in accordance with the present invention.

A) Anti-Microbial Materials Containing Atomic Disorder

At least the top layer 4, and preferably also the base layer 2, is formed in a crystalline form from anti-microbial metals with atomic disorder so as to produce an anti-microbial effect. The production of atomic disorder through physical vapour deposition techniques is described in the previous patent applications, including U.S. Pat. No. 5,454,886, and as outlined below.

The anti-microbial metal is deposited as a thin metallic film on one or more surfaces of the substrate, typically a medical device, by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to create atomic disorder in the coating as defined hereinabove. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, supra). While such conditions have been investigated in the art, they had not been linked to enhanced solubility of the coatings so-produced prior to Applicants inventions.

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working (or ambient) gas pressure, i.e. for vacuum evaporation: e-beam or arc evaporation, greater than 0.01 mT, gas scattering evaporation (pressure plating) or reactive arc evaporation, greater than 20 mT; for sputtering: greater than 75 mT; for magnetron sputtering: greater than about 10 mT; and for ion plating: greater than about 200 mT; and maintaining the angle of incidence of the coating flux on the surface to be coated at less than about 75° C., and preferably less than about 30°

The metals used in the coating are those known to release ions etc. having an anti-microbial effect, as set out above. For most medical devices, the metal must also be biocompatible. Preferred metals include the noble metals Ag, Au, Pt, Pd, and Ir as well as Sn, Cu, Sb, Bi, and Zn or alloys or compounds of these metals or other metals. Most preferred is Ag or Au, or alloys or compounds of one or more of these metals.

A thin film is formed on at least a part of the surface of the substrate/medical device. For economic reasons, the film has a thickness no greater than that needed to provide release of metal ions on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The anti-microbial effect of the material so produced is achieved when the coated substrate is brought into contact with an alcohol or a water based electrolyte such as, a body fluid or body tissue, thus releasing metal ions, atoms, molecules or clusters. The concentration of the metal species which is needed to produce an anti-microbial effect will vary from metal to metal. Generally, anti-microbial effect is achieved in body fluids such as plasma, serum or urine at concentrations less than about 0.5–5 $\mu g/ml$.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at $T/T_m<0.5$ and a working gas pressure of about 7 mTorr releases approximately ⅓ of the silver ions that a film deposited under similar conditions, but at 30 mTorr, will release over 10 days. Films that are created with an intermediate structure (ex. lower pressure, lower angle of incidence etc.) have Ag release values intermediate to these values as determined by bioassays. This then provides a method for producing controlled release metallic coatings in accordance with this invention. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 15 mTorr) for 50% of the deposition time and high (ex. 30 mTorr) for the remaining time, has a rapid initial release of metal ions, followed by a longer period of slow release. This type of coating is extremely effective on devices such as urinary catheters for which an initial rapid release is required to achieve immediate anti-microbial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable ΔT, that the temperature differential between the substrate temperature during deposition and the ultimate temperature of use, will vary from metal to metal. For the most preferred metals of Ag and Au, preferred substrate temperatures of −20 to 200° C., more preferably −10° C. to 100° C. are used.

Atomic order may also be achieved, in either or both of the base and top layers 2, 4 in accordance with the present invention, by preparing composite metal materials, that is materials which contain one or more anti-microbial metals in a metal matrix which includes atoms or molecules different from the anti-microbial metals.

Our preferred technique for preparing a composite material is to co- or sequentially deposit the anti-microbial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the anti-microbial metals, which results in atomic disorder during deposition. Alloys of this kind can also serve to reduce atomic diffusion and thus stabilize the disordered structure. Thin film deposition equipment with multiple targets for the placement of each of the anti-microbe and inert metals is preferably utilized. When layers are sequentially deposited the layer(s) of the inert metal(s) should be discontinuous, for example as islands within the anti-microbial metal matrix. The final ratio of the anti-microbial metal(s) to inert metal(s) should be greater than about 0.2. The most preferable inert metals are Ti, Ta, Zn and Nb. It is also possible to form the anti-microbial coating from oxides, carbides, nitrides, sulphides, borides, halides or hydrides of one or more of the anti-microbial metals and/or one or more of the inert metals to achieve the desired atomic disorder.

Another composite material within the scope of the present invention is formed by reactively co- or sequentially depositing, by physical vapour techniques, a reacted material into the thin film of the anti-microbial metal(s). The reacted material is an oxide, nitride, carbide, boride, sulphide, hydride or halide of the anti-microbial and/or inert metal, formed in situ by injecting the appropriate reactants, or gases containing same, (ex. air, oxygen, water, nitrogen, hydrogen, boron, sculpture, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final ratio of anti-microbial metal(s) to reaction product should be greater than about 0.2. Air, oxygen, nitrogen and hydrogen are particularly preferred reactants.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

It may be advantageous, prior to depositing an anti-microbial in accordance with the present invention, to provide an adhesion layer on the substrate or medical device to be coated, as is known in the art. For instance, for a latex device, a layer of Ti, Ta or Nb may be first deposited to enhance adhesion of the subsequently deposited anti-microbial coating. If Ta is used, a barrier layer such as tantalum oxide formed by anodization may be needed, as set out above.

2. Wound Dressings

Figure 2:
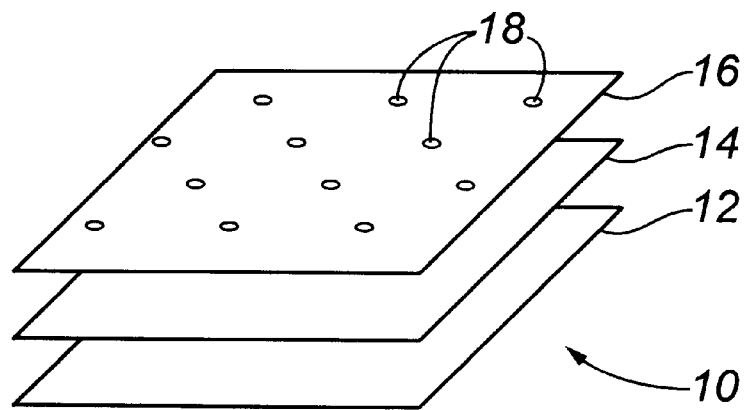
FIG. 2 is a schematic sectional figure of a three layer wound dressing in accordance with the present invention.

The wound dressing in accordance with the invention includes at least two, and preferably at least three layers, laminated together by ultrasonic welding. A three layer wound dressing in accordance with the invention is shown generally at 10 in FIG. 2 to include a first layer 12, which will be wound facing in use, a second layer 14, which preferably forms an absorbent core, and a third, optional layer 16, which forms the outer layer. The layers 12, 14 (and optionally 16) are laminated together by ultrasonic welds 18 at intermittent locations across the dressing 10.

A) Wound Facing Layer

The first layer 12 of the wound dressing 10 is formed of a perforated, preferably non-adherent material which allows for fluids to penetrate or diffuse therethrough in either or both directions. The perforated material may be formed of a woven or non-woven, non-woven being preferred, fabric such as cotton, gauze, a polymeric film such as polyethylene, nylon, polypropylene or polyester, an elastomer such as polyurethane or polybutadiene elastomers, or a foam such as open cell polyurethane foam. Exemplary perforated, non adherent materials useful for the wound dressing include non-woven meshes such as DELNET™ P530, which is a non-woven wound veil formed of high density polyethylene using extrusion, embossing and orientation processes, produced by Applied Extrusion Technologies, Inc. Of Middletown, Del., USA. This same product is available as Exu-Dry CONFORMANT 2™ Wound Veil, from Frass Survival Systems, Inc., Bronx, N.Y., USA as a subset of that company's Wound Dressing Roll (Non-Adherent) products. Other usefull non-woven meshes include CARELLE™ or NYLON 90™, available from Carolina Formed Fabrics Corp., N-TERFACEP™, available from Winfield Laboratories, Inc., of Richardson, Tex., USA. Exemplary woven meshes may be formed from fibreglass or acetate, or cotton gauze. An exemplary hydrophilic polyurethane, foam is HYPOL™, available from W.R. Grace & Co., New York, N.Y., USA.

As set out more fully below in respect of the ultrasonic welding technique, at least one of the first and wound layers 12, 14 is formed from a polymeric material which is attributable to ultrasonic welding, that is which will melt on the application of localized heat and then fuse the layers together on cooling.

B) Absorbent Layer

The second, absorbent layer is formed from an absorbent material for absorbing moisture from the wound, or as in the case of a burn wound dressing, for holding moisture next to the wound. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers; such as rayon, polyester, rayon/polyester, polyester/cotton, cotton and cellulose fibers. Exemplary are creped cellulose wadding, an air felt of air laid pulp fibers, cotton, gauze, and other well known absorbent materials suitable for wound dressings.

C) Outer Layer

The third layer 16 of the wound dressing 10 is optional, but is preferably included to regulate Moisture loss, or to art as a barrier layer (for example for moisture, oxygen penetration), to carry an anti-microbial coating, or alternatively to act as an adhesive layer to anchor the wound dressing around the wound. In the case of burn wound dressings, the third layer 16 is preferably formed of perforated, non-adherent material such as used in the first layer 12. This allows moisture penetration as sterile water and the like are added.

D) Additional Optional Layers

Additional layers (not shown) may be included between or above the first, second and third layers 12, 24, 16, as is well known in wound dressings. Thus the use of the terms first, second and third layer, as used herein and in the claims is not meant to exclude such additional layers.

E) Ultrasonic Welding

The first and second layers (and preferably the third layer, if present) are laminated together at intermittent spaced locations across the dressing 10 by ultrasonic welds 18. Ultrasonic welding is a known technique in the quilting art and thus will not be discussed at length. Briefly, heat (generated ultrasonically) and pressure are applied to either side of the dressing 10 at localized spots through an ultrasonic horn so as to cause melting of at least one of the plastic materials in the first and second layers 12, 14, and the subsequent bonding together of the layers on cooling. The welds appear at localized circular spots and are preferably less than 0.5 cm in diameter. If the third layer 16 is present, the ultrasonic welding can be performed from either side of the dressing, and will bind all three layers 12, 14 and 16 together.

The use of ultrasonic welding of the layers at spaced locations has the advantage of retaining the absorbent and moisture penetration properties of the layers 12, 14, while retaining the conforming properties of the dressing. Edge seams, stitching and adhesives have the disadvantage of interfering with one or more of these desirable properties of wound dressings. Furthermore, by spacing the welds 18 at intermittent locations across the dressing, the wound dressing may be cut to smaller sizes, as needed, without causing delamination. Preferred spacing& of about 2.5 cm between welds allows the dressing to be cut down to about 2.5 cm sizes, while maintaining at least one weld to hold the laminated layers together.

F) Anti-Microbial Coatings on Wound Dressings

The wound dressing of this invention preferably includes an anti-microbial coating formed from an anti-microbial metal. The coating is applied to one or more of the layers 12, 14, 16, but is most preferably applied at least to the first, wound facing layer 12 to provide a localized anti-microbial effect next co the wound. The coating may also be applied to the outer layer 16 for additional anti-microbial effect.

The coating is most preferably formed with atomic disorder in accordance with the procedures set out above and as described in U.S. Pat. No. 5,454,886. Most preferably, the coating is formed as a multiplayer anti-microbial coating, as set above, to produce an interference colour. In this way, the coating provides not only an anti-microbial effect to limit infection, but also acts as an indicator of activation of the dressing. As the top layer of the coating is activated by contacting an electrolyte such as wound exudate, blood or added water, even minor dissolution of the anti-microbial metal results in a detectable colour change, indicating that an anti-microbial effect is being provided. If there is no colour change, additional moisture might be provided to the coating by adding water, until a colour change is detected. In the treatment of burn wounds with the wound dressing of the invention, wound exudates are usually sufficient to activate the coating. Once activated, the dressing should be maintained in a moist condition by the addition of sterile water if necessary.

G) Sterilization and Packaging of Wound Dressings

Wound dressings with anti-microbial coatings of an anti-microbial metal formed with atomic disorder are preferably sterilized without applying excessive thermal energy, which can anneal out the atomic disorder, thereby reducing or eliminating a useful anti-microbial effect. Gamma radiation is preferred for sterilizing such wound dressings, as discussed in U.S. Pat. No. 5,454,886.

It should be appreciated that the use of ultrasonic welding to laminate the layers of wound dressings with anti-microbial coatings formed from anti-microbial metals with atomic disorder is advantageous since it achieves bonding in localized spots and avoids applying heat to any significant portion of the dressing, thereby avoiding any significant reduction in the anti-microbial effect through annealing out of atomic disorder.

The sterilized wound dressings should be sealed in air tight packaging which excludes light penetration to avoid additional oxidation of the anti-microbial coating. Metallized polyester peelable pouches are preferred. The shelf life of anti-microbial wound dressings thus sealed is over one year.

H) Burn Wound Treatment

Animal and human trials with the burn wound dressing of the present invention, carrying a bi-layer anti-microbial coating formed with silver having atomic disorder, manufactured as set out above and as described in greater detail in Example 3, have shown excellent results in controlling infection. In addition, the anti-microbial metal coating has been found to improve how well the dressing handles, reducing static and adding weight to the dressing to keep it in place during treatment and wrapping. In use, the dressings are kept moist, at 100% relative humidity. Wound exudate may be sufficient in itself to maintain this humidity level. Otherwise, adding sterile water, for instance three times daily has been found to be sufficient. The wound dressing is thereafter wrapped in a known manner to keep the wound moist and clean. Dressings are changed as required for wound observation and cleaning, but need not be changed more frequently than every 24 hours, and can provide an anti-microbial effect for a much longer period of time.

I) Advantages

Advantages of such burn wound dressings against conventional burn wound treatment regimes are set out below.

i) The amount of $Ag^+$ or silver species in solution adjacent the dressing is controlled by the concentration of $Ag^+$ in equilibrium in the solution at 60–100 $\mu g/ml$, which is sufficient to provide a sustainable anti-microbial effect for a considerable period of time. The use of a 0.5% solution of silver nitrate applied 12 times daily, provides a cumulative exposure to silver ions of 61,000 $\mu g/in^2/day$ (calculated assuming an 8 ply dressing with absorptive capacity of 200 $\mu L/in^2$ per ply). A comparable calculation for silver coated dressings of this invention, assuming a wound weep maximum of 8 $ml/in^2/day$ is 800 $\mu g/in^2/day$.

ii) Compared to silver nitrate treatments, the silver coated burn wound dressings of this invention eliminates staining from silver nitrate, leaving patients and relatives less shocked by discoloration at the injury site, and reducing the cleaning costs of the hospital (for bedding, flooring etc.).

iii) With silver nitrate treatment, the $Ag^+$ ion complexes with chloride ions a the wound dressing interface to form a non anti-microbial zone. The silver coated wound dressings of this invention provide a sustained release of silver species at a controlled and non-excessive equilibrium concentration, ensuring that silver species remain available at the wound interface.

iv) The absorbent core of the wound dressing maintains a high relative humidity at the wound site, to maintain in anti-microbial effect and to minimize drying and desiccation of new cell growth. The absorbent core also provides an "anti-microbial zone" above the wound, which extends through the thickness of the dressing to create a sufficient residence/exposure time for migrating microbes to ensure that they are killed. This is unlike silver nitrate treatment in which there is no replacement of the silver ion at the wound surface after it is consumed by chloride ions or proteins (excluding the possibility of diffusion).

v) The wound dressing needs minimal to no wetting (no more than 3 times daily), limiting the hypothermia problem encountered with silver nitrate treatments which require 12 times daily wetting and the cleaning needed when silver sulphadiazine creams are used.

vi) The silver coating on the wound dressing materials has been found to be non-adherent, and thus less disruptive to wound healing than dressings that adhere, as are often used in silver nitrate treatments.

viii) The silver coated wound dressing of this invention, produced with an interference colour and a top layer which releases, silver ions etc. on contact with an electrolyte, provides a visible colour change to demonstrate that the anti-microbial metal film has been activated and that silver species are being released.

3. EXAMPLES

The invention is further illustrated by the following non-limiting examples.

Example 1

This example is included to demonstrate multilayer colour coatings on various reflective base layers covered with anti-microbial silver top layers in order to generate first and second order interference colours. Bi-layer metal coatings were produced by magnetron sputtering onto glass coverslips base layers of Ag. Ta or Au and covering with top layers of Ag under the sputtering conditions set out in Table 1. To demonstrate Al as a base layer, the top Ag layer was sputtered onto Al foil, the Ag sputtering conditions being as set out in Table 1.

TABLE 1

| Sputtering Conditions: | Base Layer | Top Layer |
|---|---|---|
| Target | 99.99% Ag, Ta, Au | 99.99% Ag |
| Target Size | 20.3 cm diameter | 20.3 cm diameter |
| Working Gas | 100 wt % Ar | 99/1 wt % Ar/O$_2$ |
| Working Gas Pressure | 40 m Torr | 40 m Torr |
| Power | 0.1 kW | 0.05 kW |
| Substrate Temperature | 20° C. | 20° C. |
| Base Pressure | 2.0 × 10$^{-6}$ Torr | 2.0 × 10$^{-6}$ Torr |
| Anode/Cathode Distance | 100 mm | 100 mm |
| Sputtering Time/Film Thickness | Ta-16 min, 220 nm<br>Ag-8 min, 200 nm<br>Au-9 min, 200 nm | 1–10 min,<br>10–100 nm |
| Voltage | Ta-193 V<br>Ag-291 V<br>Au-322 V | 295 V |

The thickness of the top layer was varied, as set out in Table 2 below. The base layers of Ag, Ta, and Au had thicknesses of 200 nm. The resulting belayed coatings had the appearance as set out in Table 2.

TABLE 2

| Top Layer Thickness: | Base Layer Ag 99/1% Ar/O$_2$ Colour: Bronze | Base Layer Ag 100% Ar Colour: Silver | Base Layer Ta 100% Ar Colour: Grey | Base Layer Au 100% Ar Colour: Gold |
|---|---|---|---|---|
| 10 nm | Bronze/Red | Pale Red | Light Grey | Yellow/Orange |
| 20 nm | Purple | Pink.Yellow | Silver | Auburn |
| 30 nm | Blue/Purple | Light Purple | Silver | Blue |
| 40 nm | Light Blue | Grey/Blue | Gold to Silver | Turquoise |
| 50 nm | Lt Blue/Yellow | Silver | Purple to Silver | Teal |
| 60 nm | Light Yellow | Light Yellow | Blue to Silver | Lt Blue/Green |
| 70 nm | Bronze | Lt Green/Yellow | Blue to Silver | Yellow |
| 80 nm | Purple | Light Pink | Olive to Grey | Green/Yellow |
| 90 nm | Purple/Pink | Pink | Olive to Grey | Olive |
| 100 nm | Aquamarine | Aqua/Pink | Pink to Grey | Lt Pink/Yellow |

The coatings formed on Ta metal changed to silver or grey within about 10 minutes of sputtering, indicating the need for a barrier layer to prevent reduction of the top layer to Ag base metal.

When a silver top layer was sputtered onto Al foil samples, under conditions as set out above, but in 96/4 wt % Ar/O$_2$ at 0.15 kW, a blue interference colour was observed.

Sputtering conditions were varied for the Ag base layer samples by changing the working gas to 96/4 wt % Ar/O$_2$, and depositing a 900 nm film, then covering with a top layer of Ag sputtered in 96/4 wt % At/O$_2$ at 0.15 kW, V=346 V, for about 1, 1.5 and 2.25 min. to achieve about 67, 100, 140 nm films. All other conditions were as set out in Table 1. Interference colours produced were purple, blue and yellow respectively.

Example 2

This example is included to demonstrate a belayed anti-microbial silver coating on a wound dressing material. A high density polyethylene wound dressing, COMFORMANT 2™ was coated with a silver base layer and a silver/oxide top layer to generate a coloured anti-microbial coating having indicator value. The coating layers were formed by magnetron sputtering under the conditions set out in Table 3.

TABLE 3

| Sputtering Conditions: | Base Layer | Top Layer |
| --- | --- | --- |
| Target | 99.99% Ag | 99.99% Ag |
| Target Size | 20.3 cm diameter | 20.3 cm diameter |
| Working Gas | 96/4 wt % Ar/O$_2$ | 96/4 wt % Ar/O$_2$ |
| Working Gas Pressure | 40 m Torr | 40 m Torr |
| Power | 0.3 kW | 0.15 kW |
| Substrate Temperature | 20° C. | 20° C. |
| Base Pressure | 3.0 × 10$^{-6}$ Torr | 3.0 × 10$^{-6}$ Torr |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

A zone of inhibition test was conducted. Mueller Hinton agar was dispensed into Petri dishes. The agar plates were allowed to surface dry prior to being inoculated with a lawn of *Staphylococcus aureus* ATCC#25923. The inoculant was prepared from Bactrol Discs (Difco, M.) Which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition–diameter of the test material in contact with the agar). The results showed a corrected ZOI of about ) 10 mm.

The coating was analyzed by nitric acid digestion and atomic absorption analysis to contain 0.24+/–0.04 mg silver per mg high density polyethylene. The coating is a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm, Silver release studies demonstrated that silver was released continuously from the coating until an equilibrium concentration of about 66 mg/L was reached (determined by atomic absorption), a level that is 50 to 100 times higher than is expected from bulk silver metal (solubility≦1mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

Example 3

This example is included to demonstrate a multiplayer burn wound dressing in accordance with the present invention. High density polyethylene mesh dressing material CONFORMANT 2™ dressing was coated with a belayed blue anti-microbial coating as set forth in Example 2, using the sputtering conditions of Table 3. Two layers of this coated dressing material were placed above and below an absorbent core material formed from needle punched rayon/polyester (SONTARA™ 8411). The first, wound facing layer of coated polyethylene was oriented with the blue coating side down, while the third, outer layer of coated polyethylene was oriented with the blue coating facing inwardly toward the absorbent core. The three layers were laminated together by ultrasonic welding to produce welds between all three layers spaced at about 2.5 cm intervals across the dressing. This allowed the wound dressing to be cut down to about 2.5 cm size portions for the treatment of smaller wounds, while still providing at least one weld in the dressing portion.

The coated dressings were sterilized using gamma radiation and a sterilization dose of 25 kGy. The finished dressing was packaged in sealed individually metallized polyester peelable pouches, and has shown a shelf life greater than 1 year in this form.

The absorptive capacity and moisture content of the finished dressing was tested to ensure that the dressing maintained the capability to absorb after coating. Packaged, sterile dressings were tested and compared to uncoated, untreated control dressings. The absorptive capacity of the test dressings was 7.36 g of distilled water and 7.32 g of 1.23 sodium nitrate, compared to absorption by the control dressings of 7.76 g and 7.45 g respectively, indicating similar uptakes by both materials. The drop penetration of the coated dressings was tested and was found not to differ from the control dressings. The moisture content was 4.1% and 3.6% for the coated dressing and for the untreated controls respectively. Based on these results, it was concluded that the coating of the present invention does not alter the moisture related properties of the dressing.

A clinical study with 30 human patients with various degree burn wounds using the above coated wound dressings has demonstrated an ability to decrease burn wound "infection" (4 org./50 biopsies for the dressing of this invention vs. 16 org./50 biopsies for silver nitrate treatment), the dressings being changed every 24 hours and being kept at 100% relative humidity by the application of sterile water 3 times daily, compared to a control burn wound treatment with 0.5% solutions of silver nitrate applied 12 times daily, dressings being changed every 24 hours. In the above, "infection" means greater than 1×10$^5$ colony forming units/g tissue.

Example 4

This example is included to demonstrate an anti-microbial material with an in situ generated top layer on contact with an alcohol or a water based electrolyte in order to cause a colour change through the generation of an interference colour. A single layer anti-microbial coating was produced by magnetron sputtering onto high density polyethylene wound dressing using the base layer as set out in Example 3, the sputtering conditions being those set out in Table 3 of Example 2. The resulting coating was about 900 nm thick and bronze in appearance. The coating was wetted with a wet fingertip touch (saliva), causing the colour of the coating to change to blue.

Without being bound by the same, it is believed that the colour change was the result of the in situ generation of a thin film meeting the description of a reflective and light transmissive top layer as set out above, over a reflective base layer, thus creating the conditions necessary for producing an interference colour. The mechanism is believed to be as follows. The water on the coating caused a change in both the thickness of the coating and the composition of a thin top layer of the coating, thereby creating a thin top layer which had a different refractive index from the underlying coating. Water from the fingertip was sufficient to displace air in the surface pores of the film (which is known from SEM to be porous), initiating both dissolution of the film and changing the refractive index of the thin layer. The blue interference colour resulted from the incident light reflecting off both the air/thin layer interface and the thin layer/base layer interface and recombining to create a changed, blue colour.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of descriptor and not of limitation. There is no intention, in using such terms and expressions, of excluding equivalents of the features illustrated and described, it being recognized hat the scope of the invention is defined and limited only by the claims which follow.

We claim:

1. A multilayer anti-microbial material comprising:
   a base layer of a partly reflective material capable of generating an inference colour when covered with a partly reflective, partly light transmissive top layer;
   a top layer formed over said base layer, said top layer being a partly reflective, partly light transmissive thin film containing at least one anti-microbial metal and having a thickness such that an interference colour is produced, said top layer having a refractive index different from that of the base layer, and the anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

2. The material of claim 1, wherein the material in the base layer is a metal selected from the group consisting of Ag, Au, Pt, Pd, Cu, Ta, Al and alloys or compounds of one or more of these metals, in a partly reflective form.

3. The material of claim 2, wherein the anti-microbial metal in the top layer is selected from the group consisting of Ag, Au, Pt, Pd, Ir, Sn, Cu, Sb, Bi, Zn, and alloys or compounds of one or more of these metals.

4. The material of claim 3, wherein the material in the base layer and the anti-microbial metal in the top layer is a metal selected from the group consisting of Au, Ag, Pt, Pd, and Cu in a partly reflective form, and is formed by vapour deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

5. The material of claim 4, wherein the metal in the base layer and top layer is Ag, Pt or Au.

6. The material of claim 4, wherein the top layer is a thin film of a composite material formed by co-, sequentially or reactively depositing the anti-microbial metal by vapour deposition in a matrix with atoms or molecules of a different material to cream atomic disorder in the matrix, said different material being selected from the group consisting of biocompatible metals, oxygen, nitrogen, hydrogen, boron, sculpture or halogens, or an oxide, nitride, carbide, boride, halide, sulphide or hydride of either or both of an anti-microbial metal or a biocompatible metal.

7. The material of claim 6, wherein the biocompatible metal is selected from the group consisting of Ta, Ti, Nb, V, Hf, Zn, Mo, Si and Al, and wherein the anti-microbial metal is selected from the group consisting of Ag, Au, Pt, Pd, and Cu.

8. The material of claim 6, wherein the anti-microbial metal is silver and said different material is one or both of silver oxide and atoms or molecules containing oxygen trapped or absorbed in the matrix.

9. The material of claim 1, whereby the top layer is less than 400 nm thick, and the base layer is at least 25 nm thick.

10. The material of claim 8, wherein the top layer is between 5 and 210 nm thick, and the base layer is at least 60 nm thick.

11. The material of claim 8, wherein the top layer is about 40–160 nm thick and the base layer is at least 300 nm thick.

12. The material of claim 1, wherein the base and top layers are provided on a medical device.

13. The material of claim 10, wherein the base and top layers are provided on a wound dressing.

14. A multiplayer, laminated wound dressing, comprising:
   a first, wound facing layer formed of a perforated, non-adherent material;
   a second layer laminated to the first layer, and being formed of an absorbent material;
   an optional third layer laminated to one or both of the first and second layers;
   at least one of the first, second and optional third layers, being formed from a plastic material; and
   the first, second and optional third layer being laminated together by ultrasonic welds spaced intermittently on the dressing so as to allow the dressing to be cut down in size without causing delamination.

15. The wound dressing of claim 14, wherein the first layer, includes a coating containing an anti-microbial metal.

16. The, wound dressing of claim 14, wherein the first layer includes a thin film containing at least one anti-microbial metal, said anti-microbial metal being formed with sufficient atomic disorder such that the thin film, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

17. The wound dressing of claim 14, wherein the first layer includes a multiplayer anti-microbial coating comprising:
   a base layer of a partly reflective material capable of generating an interference colour when covered with a partly reflective, partly light transmissive top layer;
   a top layer formed over said base layer, said top layer being a partly reflective, partly light transmissive thin film containing at least one anti-microbial metal and having a thickness such that a first or second order interference colour is produced, said top layer having a refractive index different from that of the base layer, and anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

18. The wound dressing of claim 17, wherein the multiplayer anti-microbial coating is provided on both the first and third layers, such that a colour change is delectable on either side of the wound dressing.

19. The wound dressing of claim 17, wherein the material in the base layer is a metal selected from the group consisting of Ag, Au, Pt, Pd, Cu, Ta, Al and alloys or compounds of one or more of these metals, in a partly reflective form.

20. The wound dressing of claim 19, wherein the anti-microbial metal in the top layer is selected from the group consisting of Ag, Au, Pt, Pd, Ir, Sn, Cu, Sb, Bi, Zn, and alloys or compounds of one or more of these metal.

21. The wound dressing of claim 20, wherein the material in the base layer and the anti-microbial metal in the top layer is a metal selected from the group consisting of Au, Ag, Pt, Pd, and Cu in a partly reflective form, and is formed by vapour deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

22. The wound dressing of claim 21, wherein the metal in the base and, top layer is Ag, Pt or Au.

23. The wound dressing of claim 20, wherein the top layer is a thin film of a composite material formed by co-, sequentially or reactively depositing the anti-microbial metal by vapour deposition in a matrix with atoms or molecules of a different material to create atomic disorder in the matrix, said different material being selected from the group consisting of biocompatible metals, oxygen, nitrogen, hydrogen, boron, sculpture or halogens, or an oxide, nitride, carbide, boride, halide, sulphide or hydride of either or both of an anti-microbial metal or a biocompatible metal.

24. The wound dressing of claim 23, wherein the biocompatible metal is selected from the group consisting of Ta, Ti, Nb, V, Hf, Zn, Mo, Si and Al, and wherein the antimicrobial metal is selected from the group consisting of Ag, Au, Pr, Pd, and Cu.

25. The wound dressing of claim 23, wherein the antimicrobial metal is silver and said different material is one or both of silver oxide and atoms or molecules containing oxygen trapped or absorbed in the matrix.

26. The wound dressing of claim 17, wherein the top layer is less than 400 nm thick, and the base layer is at least 25 nm thick.

27. The wound dressing of claim 21, wherein the top layer is between 5 and 210 nm thick, and the base layer is at least 60 nm thick.

28. The wound dressing of claim 25, wherein the top layer is about 40–160 nm thick and the base layer is at least 300 nm thick.

29. The wound dressing of claim 25, wherein the material in the base layer is a metal selected from the group consisting of Au, Ag, Pt, Pd, and Cu in a partly reflective form, and is formed by vapour deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

30. The wound dressing of claim 29, wherein the first and optional third layers are formed from a non-woven, perforated, non-adherent high density polyethylene material.

31. The wound dressing of claim 30, wherein the second layer is formed from a non-woven, absorbent rayon/polyester material.

32. A process for producing a multilayer anti-microbial material capable of indicating exposure to an alcohol or water based electrolyte, comprising:

providing a base layer of a partly reflective material capable of generating an interference color when covered with a partly reflective, partly light transmissive top layer;

providing a top layer over said base layer, said top layer being a partly reflective, partly light transmissive thin film containing at least one anti-microbial metal and having a thickness such that an interference color is produced, said top layer having a refractive index different from that of the base layer, and said antimicrobial metal being formed with sufficient atomic disorder such that the top layer, in contact with an alcohol or water based electrolyte, releases ions, atomos, molecules or clusters of the antimicrobial metal into the alcohol or water based electrolyte at a concentration sufficient to provide a localized antimicrobial effect on a sustainable basis.

33. The process of claim 32, wherein the material in the base layer is a metal selected from the group consisting of Ag, Au, Pt, Pd, Cu, Ta, Al, and alloys or compounds of one or more of these metals, in a partly reflective form.

34. The process of claim 33, wherein the anti-microbial metal in the top layer is selected from the group consisting of Ag, Au, Pt, Pd, Ir, Sn, Cu, Sb, Bi, Zn, and alloys or compounds of one or more of these metals.

35. The process of claim 34, wherein the material in the base layer and the anti-microbial metal in the top layer is a metal selected from the group consisting of Ag, Au, Pt, Pd, and Cu, in a partly reflective form, and is formed by vapor deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

36. The process of claim 35, wherein the metal in the base and top layer is Ag, Pt or Au.

37. The process of claim 35, wherein the top layer is a thin film of a composite material formed by co-, sequentially or reactively depositing the anti-microbial metal by vapor deposition in amatrix with atoms or molecules of a different material to create atomic disorder in the matrix, said different material being selected from the group consisting of biocompatible metals, oxygen, nitrogen, hydrogen, boron, sulphur or halogens, or an oxide, nitride, carbide, boride, halide, sulphide or hydride of either or both of an antimicrobial metal or biocompatible metal.

38. The process of claim 37, wherein the biocompatible metal is selected from the group consisting of Ta, Ti, Nb, V, Hf, Zn, Mo, Si, and Al, and wherein the anti-microbial metal is selected from the group consisting of Ag, Au, Pt, Pd and Cu.

39. The process of claim 37, wherein the anti-microbial metal is silver and said different material is one or both of silver oxide and atoms or molecules containing oxygen trapped or absorbed in the matrix.

40. The process of claim 32, wherein the top layer is less than 400 mm thick, and the base layer is at least 25 mm thick.

41. The process of claim 37, wherein the top layer is between 5 and 210 nm thick, and the base layer is at least 60 nm thick.

42. The process of claim 39, wherein the top layer is about 40–160 nm thick, and the base layer is at least 300 nm thick.

43. The process of claim 32, wherein the base and top layers are provided on a medical device.

44. The process of claim 41, wherein the base and top layers are provided on a wound dressing.

* * * * *